US011538563B2

(12) United States Patent
Goldberg

(10) Patent No.: US 11,538,563 B2
(45) Date of Patent: Dec. 27, 2022

(54) FACILITATING HEALTH MANAGEMENT OF SUBJECTS

(71) Applicant: Ideal Life Inc., Toronto (CA)

(72) Inventor: Jason Goldberg, Toronto (CA)

(73) Assignee: Ideal Life Inc., Toronto (CA)

( * ) Notice: Subject to any disclaimer, the term of this patent is extended or adjusted under 35 U.S.C. 154(b) by 317 days.

(21) Appl. No.: 16/991,847

(22) Filed: Aug. 12, 2020

(65) Prior Publication Data

US 2020/0373010 A1    Nov. 26, 2020

Related U.S. Application Data

(63) Continuation of application No. 14/560,348, filed on Dec. 4, 2014, now Pat. No. 10,747,849, which is a continuation of application No. 13/851,295, filed on Mar. 27, 2013, now Pat. No. 8,930,215, which is a continuation of application No. 12/509,119, filed on Jul. 24, 2009, now Pat. No. 8,423,378.

(60) Provisional application No. 61/083,268, filed on Jul. 24, 2008.

(51) Int. Cl.
| | |
|---|---|
| *G16H 80/00* | (2018.01) |
| *G16H 10/60* | (2018.01) |
| *G16H 40/67* | (2018.01) |
| *G06Q 50/22* | (2018.01) |

(52) U.S. Cl.
CPC ............ *G16H 10/60* (2018.01); *G06Q 50/22* (2013.01); *G16H 40/67* (2018.01); *G16H 80/00* (2018.01)

(58) Field of Classification Search
CPC ..... A61B 5/0022; A61B 5/0002; G16H 80/00
See application file for complete search history.

(56) References Cited

U.S. PATENT DOCUMENTS

| | | | |
|---|---|---|---|
| 4,731,726 | A | 3/1988 | Allen, III |
| 5,390,238 | A | 2/1995 | Kirk et al. |
| 5,576,952 | A | 11/1996 | Stutman et al. |
| (Continued) | | | |

OTHER PUBLICATIONS

Robinson, Brian, "VA improves telehealth access", Federal Computer Week; Falls Church, Jan. 7, 2002; vol. 16; issue 1; p. 30.

*Primary Examiner* — John A Pauls
(74) *Attorney, Agent, or Firm* — Jon E. Gordon; Haug Partners LLP

(57) ABSTRACT

A peer system of subjects with health-related issues is formed based on an association of subjects and a particular type of electronic device or devices which provides information related to a specific health-related issue or issues obtained from particular subjects. By means of such associations, subjects can transmit to and receive messages from other subjects associated with the same type of electronic device. One way to associate subjects with health-related issues is through an association of a subject with a type or types of sensors. For example, each monitoring device may be associated with a subject, and the type or types of sensor or sensors may be associated with the subject and/or monitoring device. Devices, systems, methods and computer program products may be provided leveraging this association for various applications, e.g., management of the health care of subjects, peering among subjects with a common heath-related issue or issues, advertising, research and other applications involving such subjects.

1 Claim, 7 Drawing Sheets

(56) References Cited

U.S. PATENT DOCUMENTS

| | | |
|---|---|---|
| 5,704,366 A | 1/1998 | Tacklind et al. |
| 5,772,586 A | 6/1998 | Heinonen et al. |
| 5,822,715 A | 10/1998 | Worthington et al. |
| 5,827,180 A | 10/1998 | Goodman |
| 5,832,448 A | 11/1998 | Brown |
| 5,879,375 A | 3/1999 | Larson, Jr. et al. |
| 5,897,493 A | 4/1999 | Brown |
| 5,956,501 A | 9/1999 | Brown |
| 5,997,476 A | 12/1999 | Brown |
| 6,024,699 A | 2/2000 | Surwit et al. |
| 6,050,940 A | 4/2000 | Braun et al. |
| 6,101,478 A | 8/2000 | Brown |
| 6,168,563 B1 | 1/2001 | Brown |
| 6,196,970 B1 | 3/2001 | Brown |
| 6,221,010 B1 | 4/2001 | Lucas |
| 6,233,539 B1 | 5/2001 | Brown |
| 6,246,992 B1 | 6/2001 | Brown |
| 6,248,065 B1 | 6/2001 | Brown |
| 6,270,455 B1 | 8/2001 | Brown |
| 6,302,844 B1 | 10/2001 | Walker et al. |
| 6,368,273 B1 | 4/2002 | Brown |
| 6,375,614 B1 | 4/2002 | Braun et al. |
| 6,379,301 B1 | 4/2002 | Worthington et al. |
| 6,381,577 B1 | 4/2002 | Brown |
| 6,454,705 B1 | 9/2002 | Cosentino et al. |
| 8,165,893 B1 | 4/2012 | Goldberg et al. |
| 2002/0097150 A1 * | 7/2002 | Sandelman ......... G06F 11/0748 340/506 |
| 2004/0019505 A1 | 1/2004 | Bowman et al. |
| 2004/0133776 A1 | 7/2004 | Putzolu |
| 2005/0026518 A1 | 2/2005 | Bolster |
| 2005/0206518 A1 * | 9/2005 | Welch ................. A61B 5/0024 340/539.12 |
| 2008/0097908 A1 * | 4/2008 | Dicks .................... A61B 5/1112 705/50 |
| 2008/0097914 A1 | 4/2008 | Dicks |
| 2008/0177570 A1 | 7/2008 | Craine |
| 2009/0125333 A1 * | 5/2009 | Heywood ............ A61B 5/0002 705/3 |

* cited by examiner

SUBJECT TABLE

| USER ID | DEVICE ID | USER NAME | ADDRESS | TEL. NO. | TEL. NO. | E-MAIL ADDRESS | OTHER (Medical information, demographic, SSN, Password, PIN, Insurance) |
|---|---|---|---|---|---|---|---|

↳ 300

DEVICE TABLE

| DEVICE ID | USER ID | SENSOR TYPE | ORGANIZATION GROUP | ORGANIZATION GROUP | MESSAGE GROUP FLAG | MESSAGE GROUP FLAG |
|---|---|---|---|---|---|---|

↳ 302

CARE GIVER TABLE

| CARE GP ID | USER NAME | DEVICE ID | SENSOR TYPE |
|---|---|---|---|

↳ 304

MESSAGE GROUP TABLE

| MESSAGE GP ID | DEVICE ID | SENSOR TYPE | USER NAME | ORGANIZATION ID | OTHER |
|---|---|---|---|---|---|
| 310 | 312 | 314 | 316 | 318 | |

| Device ID | Message GPID | Sensor Type 0001 | Sensor Type 0002 | ... | Sensor Type XXXX | Organization ID 0001 | Organization ID 0002 | ... | Organization ID XXXX |
|---|---|---|---|---|---|---|---|---|---|
| 0001 | 0001 | Y | N | | | Y | N | | |
| 0002 | 0002 | N | Y | | | Y | N | | |
| 0003 | 0003 | Y | N | | | N | Y | | |
| 0004 | 0001 | Y | Y | | | Y | N | | |
| 0005 | 0004 | Y | N | | | N | Y | | |
| 0006 | 0005 | N | Y | | | N | Y | | |
| 0007 | 0005 | N | Y | | | N | Y | | |
| . | | | | | | | | | |
| . | | | | | | | | | |
| . | | | | | | | | | |
| XXXX | | | | | | | — | | |

FIG. 7

FACILITATING HEALTH MANAGEMENT OF SUBJECTS

RELATED APPLICATIONS

This application is a continuation of application Ser. No. 14/560,348, filed Dec. 4, 2014, which is a continuation of application Ser. No. 13/851,295, filed Mar. 27, 2013, now U.S. Pat. No. 8,930,215 issued Jan. 6, 2015, which is a continuation of application Ser. No. 12/509,119, filed Jul. 24, 2009, now U.S. Pat. No. 8,423,378, issued Apr. 16, 2013, which claims the benefit of and priority to provisional Application No. 61/083,268, filed Jul. 24, 2008. This application also claims the benefit of and priority to provisional Application No. 61/083,268. The entire disclosures of application Ser. Nos. 14/560,348, 13/851,295, 12/509,119 and 61/083,268 are incorporated herein by reference.

Some of the subject matter disclosed herein is disclosed in application Ser. No. 10/892,520 filed Jul. 15, 2004; Ser. No. 10/913,140 filed Aug. 6, 2004; Ser. No. 10/963,205 filed Oct. 11, 2004; Ser. No. 11/108,355 filed Apr. 18, 2005; and Ser. No. 11/356,739 filed on Feb. 16, 2006 (each "a cited application" and collectively "the cited applications"). The disclosures of all of these applications are incorporated herein by reference except for subject matter that is substantively incompatible with the disclosure of this application. In addition, terms may be used differently herein, or encompass different things as used herein, than in the cited applications, and this application should not be used to interpret terms in the cited applications which stand on their own.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

BACKGROUND OF THE INVENTION

The invention disclosed herein generally relates to facilitating health management of subjects. In various embodiments, subjects are associated with an electronic device which provides health-related information with respect to the respective subject, and the electronic device can communicate with one or more other electronic devices peered based on health-related information. In various embodiments, an electronic device can receive messages originated by other electronic devices and/or sources other than an electronic device.

SUMMARY OF THE INVENTION

The ability to communicate with subjects known to be associated in some way with a specific health-related issue or issues can provide unprecedented opportunities, e.g., for health management, peering, advertising, research, motivation, competition, education and other applications. Embodiments of the invention generally provide devices, systems, methods and computer program products (computer readable medium) leveraging this association for various such and other applications.

Various embodiments of the invention provide for association of subjects and health-related information, e.g., via a particular type of electronic device(s) or sensor(s) which provide health-related information with respect to a respective subject and/or a characteristic or characteristics of health-related information and/or other information such as information relating to the subject.

Aspects of the invention include one or more of the following: obtaining health-related information from subjects through use of electronic devices and in other ways; storing the health-related information and other information, e.g., in one or more databases; providing or otherwise making available at least some of the health-related and other information to subjects and other parties; messaging over a network between and among selected subjects using the electronic devices based on health-related information; a messaging system including the electronic devices; and communication over the network of the health-related and other information from, to and/or between the electronic devices associated with subjects.

In various embodiments, one or more electronic devices are associated with a subject. Each electronic device has identifying information associated therewith and each electronic device is associated at least one sensor which provides to the electronic device health-related information relating to the respective subject. A plurality of first electronic devices have associated therewith a first type of sensor and a plurality of second electronic devices have associated therewith a second type of sensor different from the first sensor type. In various embodiments, a relationship is provided of identifying information and sensor type for each of the plurality of electronic devices. Messages are routed over a network at least to and from electronic devices based on one or more of the stored relationships.

Messaging can include one or more of the following and other activities: composing a message on an electronic device, storing a message on an electronic device and/or in a data storage device accessible by at least one computer other than the electronic device; transmitting a message from an electronic device; routing a message; receiving a message on an electronic device; and displaying a message on an electronic device. "Message" is meant herein in a broad sense and, unless the context indicates otherwise, encompasses text and/or graphics and/or audio.

"Health" and "health care" are meant in a broad sense, and encompass well being, fitness, and other things even though such things may be enumerated separately from uses of "health" and "health care," etc. "Health-related information," is meant herein in a broad sense and unless the context indicates otherwise comprises information relating to health, well-being, fitness, disease, sickness, treatment, medical condition, diagnosis, etc., and includes medical information, physiological information, measurements, etc. Health-related information includes information related to: e.g., blood pressure; heart rate; body temperature; weight; EKG; EEG; glucose level (blood sugar); respiratory capacity (e.g., PEAK flow); exercise, e.g., distance ran, walked, pedaled, on the ground or a on treadmill or on a bicycle or skates, etc., or steps climbed; substances and/or chemical presence or level (e.g., drugs, proteins, hormones, compounds, chemicals and things which may be found in a subject's body, blood, body fluids, etc.); levels of remaining and/or usage of medicine and/or consumable items such as insulin remaining in an insulin pump, bronchodilator medicine in a nebulizer or glucose test strips, etc.; therapeutic effect; efficacy, compliance; tracking; etc. Health-related information may be in the form of measurement and test data, diagrams, evaluations, health records, charts, various scans, news, current events, alerts, messages, historical data, statistical data, and in other forms.

The term "subject" is used herein in a broad sense and unless the context indicates otherwise encompasses a patient or individual with a health-related issue. The invention has application to groups of subjects and/or to organizations relating to health care and/or management, e.g., care groups, (e.g., managed care groups, HMOs, HIPSs, etc.), care provider groups (e.g., medical groups, medical offices, clinics, hospitals, fitness centers, nutritionists, weight management centers, etc.), fitness program providers, weight management program providers, insurers, payors, health plans, etc. Care groups and/or provider groups may provide for and/or arrange health care and/or management for members by health care professionals such as doctors, where the group may be responsible for paying the health care professionals for the health care service and the group charges or is paid on a per member basis. Such an arrangement may, for example, encourage groups to deliver the health care services at an aggregated cost that is low compared to the aggregated amounts paid to the groups. For example, fees to be paid to professionals may be pre-agreed for given health care services, and equal or substantially equal fees may be charged to all or some members of the group.

Groups may be assembled based on suitable criteria. The invention also has application to groups of subjects and/or to organizations not relating to health care and/or management, but which form groups of subjects on the basis of criteria disclosed herein. For example, an Internet service provider may assemble subjects with electronic devices into fitness or weight loss groups, etc.

In various embodiments, an electronic device, which provides at least some of the health-related information discussed herein is associated with a subject and can be operated by or on behalf of a subject, e.g., by a service provider, health care provider, care giver, family member, etc. In various embodiments, such electronic devices may be sized to be easily portable and carried by subjects, but need not be, and/or may be used in a any suitable place, e.g., a subject's home or work facility, a service provider's facility, a health care provider's facility, a care giver's facility, outdoors, fitness centers, and in other places. In various embodiments, health-related information may be provided by the electronic device to at least one computer, e.g., of a service provider, or care group or care provider group or some other organization, etc., over any suitable open or closed, public or private network, e.g., a communications system, intranet, Internet, LAN, WAN, cellular telephone system, radio system, PSTS or POTs telephone systems, paging systems, satellite systems, etc. Such networks, groups and/or organizations, etc., may be subscription based or free, open or closed, private or public.

In various embodiments, electronic devices provide time information along with health-related information, e.g., the date and time of day that health-related information was received by an electronic device. In various embodiments, electronic devices may also obtain or determine position information, e.g., via GPS. Date, time, and/or position information provide still more opportunities for messaging content and association, real time applications, and still more opportunities for leveraging the associations disclosed herein.

An electronic device operated by (or on behalf of) a subject useful for obtaining health-related information is referred to herein as a "monitoring device" for ease of reference and without intending to limit the types of electronic devices that may be used. Such an electronic device may include portable and desktop devices, e.g., monitoring devices as described, for example, in the cited applications, PDAs, laptop computers, cellular phones, desktop computers (e.g., PCs), etc. A monitoring device used to obtain health-related information from subjects is meant in a broad sense and unless the context indicates otherwise encompasses electronic devices operated by (or on behalf of) a subject which receive information from one or more types of sensors, whether of an intrusive or non-intrusive nature, or directly or indirectly, from a subject. Such monitoring devices can include a user interface, e.g., an input device or devices such as a keypad, keyboard, touch screen, pointing device and/or voice recognition, etc., and a display device or devices such as an LCD, LED and/or plasma device, etc. The specific type of monitoring device is not critical, and any suitable monitoring device, and any suitable communication protocol for communicating over the network may be used. An example of a non-intrusive direct sensor is a blood pressure cuff, and an example of an indirect sensor is a glucose monitor which tests a blood sample obtained, e.g., in an intrusive manner, e.g., by pricking a finger.

In various embodiments of the invention, membership of a subject in a group or sub-group for messaging purposes is based on a common or similar heath-related issue or issues of all subjects in the particular group or sub-group, who each operate (or have operated for them) a monitoring device or devices. One way to associate subjects with health-related issues is through an association of a subject with a type or types of sensors (which provide a type or types of health-related information). For example, each monitoring device may be identified, e.g., relatively or absolutely uniquely, and associated with a subject, e.g., a single subject, and associated with the type or types of sensor or sensors associated with the subject and/or monitoring device. A sensor type, or the type of information provided thereby, may be used to identify or classify a health related issue.

Because of privacy and HIPAA requirements and concerns in certain applications, participation in a messaging group can be made voluntary, and subjects would be provided with the opportunity to opt out of (or opt into) one or more peer messaging groups. In addition, the identity of participants may be maintained anonymous, either on a mandatory or voluntary basis. One way to implement anonymity is by assigning or allowing participants to select, subject to uniqueness, device addresses for messaging purposes that do not reveal the identity of the participant. For example, the Internet email address format may be adopted where the user name does not reveal the identity of the participant. The user name may, e.g., be a pseudo name, or any unique set of characters permitted by the naming convention.

However, in some applications HIPAA may not be applicable, such as in a fitness program based on subjects performing physical exercise, such as running. However, even in such applications it may be desirable to at least partially implement a HIPAA requirement or requirements.

According to some embodiments, monitoring devices provide messages destined for other monitoring devices so that subjects may communicate with each other over a network using the monitoring devices. A message may be composed on a monitoring device, e.g., through use of its input device. For example, a keypad or keyboard, or buttons, or touch or pointing device may be used to input and/or select text and/or graphics stored or presented by the monitoring device. In accordance with some embodiments, only subjects sharing a common or related health-related issue are permitted to communicate with each other. One way to implement such embodiments is to associate subjects into a message group based on, e.g., monitoring device identifications and/or subject identifications, etc., that may be unique, either on a relative or absolute basis, e.g., relative to a care group, or on a system wide or other absolute basis. Associating subjects with a common or related health-related issue may be based on the type of sensor(s) associated with respective monitoring devices, and/or information obtained or collected from subjects, and/or examination of subjects, and/or from questionnaires, etc.

According to some embodiments, monitoring devices may be easily portable and may be easily worn (e.g., on a wrist, belt, etc.) or carried (e.g., in a pocket, pocketbook, etc.). Some embodiments include an intermediary transmission device which communicates with one or more monitoring devices, and over a network, with at least one computer. In embodiments using an intermediary transmission device, such transmission devices may be stationary or movable, e.g., easily portable, and may be placed in any convenient location in a home, office, play, exercise or other facility. Monitoring devices and an associated transmission device may be located in a same building, facility, complex, etc., or sub-part thereof (e.g., a house, a room, apartment or office in a building, facility, complex, etc.). In this respect, a monitored subject may move freely about the building, facility or complex, and information will be transmitted between monitoring devices and an intermediary transmission device. A monitored subject may locate a monitoring device, such as a scale, in one room and the intermediary transmission device in another, e.g., convenient to a communications port (telephone jack, internet terminal, etc.).

According to some embodiments, each of the monitoring devices is associated with at least one sensor, e.g., a sensor which provides health-related information. Such sensors may provide a wide variety of health-related information such as, blood pressure; heart rate; body temperature; weight; EKG; EEG; glucose level (blood sugar); respiratory capacity (e.g., PEAK flow); exercise, e.g., distance ran, walked, pedaled, on the ground or a on treadmill or bicycle or skates, etc., or steps climbed; substances and/or chemical presence or level (e.g., drugs, proteins, hormones, compounds, chemicals and things which may be found in a subject's body, blood, body fluids, etc.); levels of remaining and/or usage of medicine and/or consumable items such as insulin remaining in an insulin pump, bronchodilator medicine in a nebulizer or glucose test strips, etc.; therapeutic effect; efficacy, compliance; tracking; etc. In various embodiments, a plurality of monitoring devices are associated with a first type of sensor, e.g., a blood pressure sensor or cuff, and a plurality of monitoring devices are associated with a second type of sensor, e.g., a weight sensor or scale. According to various embodiments, monitoring devices associated with the same type of sensor can communicate with each other (e.g., in a two-party or multi-party basis, or sub-group basis, etc.) over the network, as managed by a computer of a service provider, care giver group, or an organization, etc., e.g., the at least one computer referred to above. For example, a monitoring device associated with a blood pressure type sensor may communicate with another monitoring device associated with a blood pressure type sensor, but a monitoring device not associated with a blood pressure type sensor may not communicate with another monitoring device that is not associated with a blood pressure type sensor (or sensor type which senses a parameter related to a condition to which blood pressure is also related). However, communication between monitoring devices associated with a blood pressure type sensor may be restricted to members of an organizational group, demographic group, geographic group, etc., a subset of all subjects associated with the same type of sensor, e.g., based on membership in an organization, demographics, etc.

In various embodiments, data is stored in at east one storage device, e.g., in at least one database, from which data may be obtained and to which data may be provided, by the at least one computer referred to above. For example, the storage device(s) may comprise electronic memory, magnetic memory, optical memory, ROM, RAM, tape, etc., store subject information, health-related information and other information. The at least one computer may, over the network, receive information from and provide information to monitoring devices, and may also provide information to and receive information from other persons and entities, e.g., family members, interested individuals such as care givers, health proxies, or any other person authorized to receive such information.

According to various embodiments, at least one database and the at least one computer may be provided. For example, they may be provided by and/or operated by a service provider, etc., who provides the functionality and/or services described herein including that of the messaging system. According to various embodiments, the service provider may provide the monitoring devices and other equipment. In some embodiments, the service provider may be a care group and/or care provider group, or another type of organization such as an Internet provider, and in some embodiments, the service provider may provide the functionality, services and/or equipment for one or more groups.

The at least one computer may be involved with managing and/or documenting the health, medical condition, well being, and/or fitness, etc., of individual subjects or in general, and/or managing and/or documenting drug tests, clinical evaluations, etc. Thus, the at least one computer may collect information from individual subjects, and analyze and process such information in the nature of a health-related database for a specific health-related issue or condition. Information may be provided, e.g., for research, analysis or other purposes stripped of personal patient information. Subjects may enter demographic information and other information into the database via the monitoring devices, e.g., for analysis and research purposes.

The ability to identify subjects with specific health-related issues with such precision allows unprecedented targeting of the population at large of subjects having monitoring devices, e.g., for advertising and research, in the health and/or other fields. Subject information may be used by the at least one computer for targeted messages, e.g., informational messages, health related news, alerts, advertising, social messages, educational messages, messages with health-related information, statistical information, medical records, messages offering encouragement or competition, etc. For example, where a monitoring device supplies blood pressure information, the information may be used to identify a subject as a candidate for a hypertension drug, etc., and the subject supplied with information or advertising regarding hypertension drugs. Similarly, such a subject may be supplied with an alert of an environmental condition, such as extreme high or low temperatures, or ozone content using member position or geographical information. A monitoring device that supplies respiratory information may identify the associated member as a candidate for an alert of high ozone content, or high air pollution levels, etc. A monitoring device that supplies exercise information, e.g., from a pedometer or treadmill, may identify the associated subject to receive race event information, etc.

Advertisers, researchers and others may interactively collect information or otherwise interact with subjects identified, as discussed herein, to have a specific health-related issue or issues. Participation by subjects may be encouraged by offering and providing rewards, e.g., payment, for a subject to take a desired action, e.g., specific to the type of monitoring device used by the subject. Such an action may include taking a measurement using a specific type of monitoring device, answering a question, e.g., via the monitoring device, visiting a health care professional, for exercising, etc. Health care management may also take advantage of such interactivity by providing the reward(s).

Groups and/or subgroups of subjects associated with the same type of monitoring device may be formed based on specific information related to specific subjects such as demographics or extent of a condition, or goals, or location, or information provided by subjects in response to queries, etc. For example, male and female subjects in a weight management program may be assigned to different groups or subgroups. Also, subjects at different weight levels, or subjects with different weight loss goals, may be assigned to different groups. In another example, marathon runners may be identified from the type of sensor used and health-related information, and assigned to a marathon running group. Similarly, diabetic subjects may be identified by glucose type sensors and health-related information and grouped or sub-grouped based on type I or type II, and subjects with blood pressure issues may be grouped or sub-grouped based on severity, or the presence of other conditions, such as a previous heart attack, or obesity, etc. Such grouping and sub-grouping can be dynamic, i.e., membership in such groups or subgroups may be real-time dynamic based, e.g., on live and/or real time data, statistical data related to data provided by a subjects monitoring device, etc. For example, statistical data can be information created from responses to queries, which may be combined with data provided by a monitoring device or devices, and/or stored data or other data.

Subjects may be peered on an individual or group basis, i.e., one to one, one to many, many to one and many to many based on a health-related issue or issues as discussed herein and other factors, e.g., associations, membership in a group or subgroup, or a subset of subjects, etc. In one embodiment, peered subjects may be organized to function as a support group for a health-related issue or issues, e.g., as a sole function of the peered group or for performing other functions as well. In one embodiment, third parties without a monitoring device may be enabled to communicate with a member or members of a messaging or peer group, e.g., a peer support group.

Messages from a monitoring device may comprise various content and themes, e.g., motivation (or encouragement), competition, educational, informational (e.g., drugs, treatments, names of doctors, hospitals, insurance plans, events, etc.), social, alerts, etc.

Various embodiments of the invention may provide for real time interaction of subjects within a group or subgroup, and/or for providing information to devices of subjects in a group as the information becomes available, e.g., in real time, or at scheduled times, etc. For example, date and time information may indicate that subjects exercise at about the same time. Such information can be used to form an exercise group that interacts in real time. For example, health-related information, e.g., distance run, speed (based on pedometer and time information or treadmill data) may be provided to members of this group for purposes of competition, motivation or encouragement, and members may message each other in real time while they are exercising, etc. Similarly, members in a weight management group or members with a diabetic condition may be provided with information and exchange messages at meal times.

In various embodiments, health-related information provided to the at least one computer by electronic devices of subjects of a group may be provided to all or selected subjects of a group as the information is received and processed by the at least one computer. With such information, members of the group may function as a support group and contact, via respective electronic devices or otherwise, subjects to offer support, encouragement, assistance, etc. Many other applications of the ability to provide real time information to members of a group with a common health issue will be apparent to those in the field.

In various embodiments groups may be formed based on health-related information, e.g., sensor type(s) and filtered by demographics, and/or geography, and/or time-related data. For example, a group may be formed of subjects whose electronic devices are associated with a blood pressure cuff, who are female and over the age of 65, who live within a certain geographic area, etc.

As disclosed herein, an electronic device may comprise a cell phone or PDA. In such and other embodiments, messages may be audio in addition to or in place of visual messages.

With respect to compliance, the user interface of a monitoring device may be used to provide and receive compliance-related information.

According to an embodiment of the invention, a system is provided, e.g., for facilitating management of health of subjects, comprising: at least one computer; and a plurality of electronic devices, wherein each electronic device includes: (a) at least one input device through use of which a message can be composed on the electronic device; (b) at least one display device that is capable of displaying a message; and (c) at least one programmed processor and memory accessible by the at least one processor. In various embodiments, the at least one processor is involved with, e.g., manages, processing of health-related information of a subject, message composition, receipt and/or display, and communicating with the at least one computer over a network. In various embodiments, associated with each electronic device is information identifying the electronic device. In various embodiments, each of the electronic devices has associated therewith at least one sensor which provides health-related information obtained from a subject to a respective electronic device. In various embodiments, a plurality of first electronic devices have associated therewith a first type of sensor and a plurality of second electronic devices have associated therewith a second type of sensor different from the first sensor type. In various embodiments, at least one database is provided that is accessed by the at least one computer, the at least one database storing at least information relating to each of the subjects and the information associated with each the electronic devices, the database being configured to associate the unique information associated with a respective electronic device with only one subject and to associate each subject with a unique destination. In various embodiments, the at least one computer is configured to (a) provide a message received from a first electronic device to a destination electronic device or devices enabled by the at least one computer based on the sensor type or types associated with the first electronic device and the destination device(s).

According to an embodiment of the invention, a method is provided, e.g., for facilitating management of health of subjects, comprising: providing each subject with a electronic device, wherein each electronic device: (a) is associated with either a first type of sensor or a second type of sensor different from the first type of sensor that each provides health-related information of the subject to the electronic device; (b) provides the health related information to at least one computer over a network; (c) receives a message composed on the electronic device through use of an input device, (c) displays a message; and (d) provides a message to and receives a message from at least one computer over the network. In various embodiments, the method includes configuring the at least one computer to which a message is provided to provide messages received from a message originating electronic device to a destination electronic device only if the two electronic devices are associated with the same type of sensor.

According to an embodiment of the invention, a system is provided, e.g., for facilitating management of health care of subjects, comprising at least one computer; at least one storage device accessible by the at least one computer; and a plurality of electronic devices, wherein each electronic device: (a) comprises a display device, an input device and a programmed processor and memory accessible thereby; (b) has associated therewith at least one of a plurality of sensors of different type which provide to the associated electronic device health-related information obtained from a subject; and (c) is configured to provide a message composed thereon through use of the input device thereof. In various embodiments, the system is configured so that the electronic devices and the at least one computer communicate over a network and send and receive information related to the health-related information provided by a respective sensor, and a message. In various embodiments, the at least one storage device stores at least information relating to each of the subjects and information associating each electronic device with each sensor associated with the respective electronic device. In various embodiments, the at least one computer is configured to provide a message received from a first electronic device to a destination electronic device or devices based on the type of sensor with which the originating and destination electronic devices are associated.

According to an embodiment of the invention, a system is provided, e.g., for facilitating heath management of subjects, comprising: a plurality of electronic devices, wherein each electronic device is associated with at least one sensor of a plurality of sensors of different types to receive sensor data therefrom and is adapted to communicate with at least one computer to provide thereto data related to the sensor data. In various embodiments, each electronic device is associated with a single subject, and comprises: an input device through use of which a message can be composed on the electronic device; and a display device that can display a message composed on or received by the electronic device. In various embodiments, the system comprises at least one computer and a computer readable medium storing computer code which causes the at least one computer to control transmission of a message received from one electronic device to at least one other electronic device based on the sensor type associated with the electronic devices. In various embodiments, each electronic device also includes a module which communicates with the at least one computer to transmit a message thereto and receive a message therefrom.

According to an embodiment of the invention, a system is provided, e.g., for facilitating heath care management of subjects, comprising: a plurality of electronic devices, wherein each electronic device is associated with at least one sensor of a plurality of sensors of different types to receive sensor data therefrom and is adapted to communicate with at least one computer to provide thereto data related to the sensor data. In various embodiments, each electronic device is associated with a single subject, and includes a display device that can display messages received by the electronic device. In various embodiments, the system includes at least one computer and a computer readable medium storing computer code which causes the at least one computer to control transmission of messages to a plurality of electronic devices based on message content and the sensor type associated with the electronic devices.

According to an embodiment of the invention, a system is provided for facilitating management of health of subjects, comprising at least one computer; at least one data storage device accessible by the at least one computer; and a plurality of electronic devices, with the electronic devices and the at least one computer communicating over a network.

In various embodiments, each electronic device has associated therewith at least one sensor which provides to a respective electronic device health-related information relating to a respective subject, a plurality of first electronic devices having associated therewith a first type of sensor and a plurality of second electronic devices having associated therewith a second type of sensor different from the first sensor type. In various embodiments, each electronic device comprises at least one input device through use of which a message can be composed on the electronic device; at least one display device that is capable of displaying messages composed on and received by the electronic device; and identifying information associated therewith by which the respective electronic device can be identified. In various embodiments, the at least one data storage device stores a relationship of identifying information and sensor type for each of the plurality of electronic devices.

In various embodiments, the at least one computer is configured to control routing of messages over the network at least to and from electronic devices based on one or more of the stored relationships. In various embodiments, the at least one computer is also configured to control routing of messages, not composed on a electronic device, from the at least one computer to a plurality of electronic devices based on one or more of the stored relationships.

According to an embodiment of the invention, a method is provided, e.g., for facilitating management of health of subjects, who each have a electronic device each having identifying information associated therewith and with which is associated at least one sensor which provides to the electronic device health-related information relating to the respective subject, wherein a plurality of first electronic devices have associated therewith a first type of sensor and a plurality of second electronic devices have associated therewith a second type of sensor different from the first sensor type. The method comprises storing a relationship of identifying information and sensor type for each of the plurality of electronic devices; and at least one computer routing messages over a network at least to and from electronic devices based on one or more of the stored relationships. Various embodiments of the electronic device may be as disclosed herein.

According to an embodiment of the invention, a system is provided for facilitating management of health of subjects, comprising: a computer system including at least one storage device that stores health-related information of a plurality of persons including health-related information of a plurality of persons arranged in at least one group in which each person in a respective group has a health-related issue in common; and a device for obtaining health-related information from each of the plurality of persons. In various embodiments, each device obtains health-related information from each of the plurality of persons for transmission over a network to the computer system and the computer system generates health-related information for transmission over the network to each device. In various embodiments, each device includes a messaging component for sending and receiving over a network or the network at least text messages originated by another device of a person within the same group or originated by the computer system.

According to some embodiments, the messages include an identifier by which the content of the message is classified, and wherein each identifier is associated with one or more types of sensors.

According to some embodiments, message content comprises advertising.

According to an embodiment of the invention, a computer readable medium or media are provided storing program code which when executed by the at least one computer and/or one or more electronic devices causes the at least one computer and/or electronic devices to perform functionality disclosed herein, e.g., methods disclosed herein.

BRIEF DESCRIPTION OF THE DRAWINGS

The figures of the accompanying drawings are meant to be exemplary and not limiting. Like references in the figures are intended to refer to like or corresponding parts.

FIG. 5 depicts embodiments of data structures according to an embodiment of the invention.

FIG. 7 depicts an embodiment of a data structure according to an embodiment of the invention.

DETAILED DESCRIPTION

Figure 1:
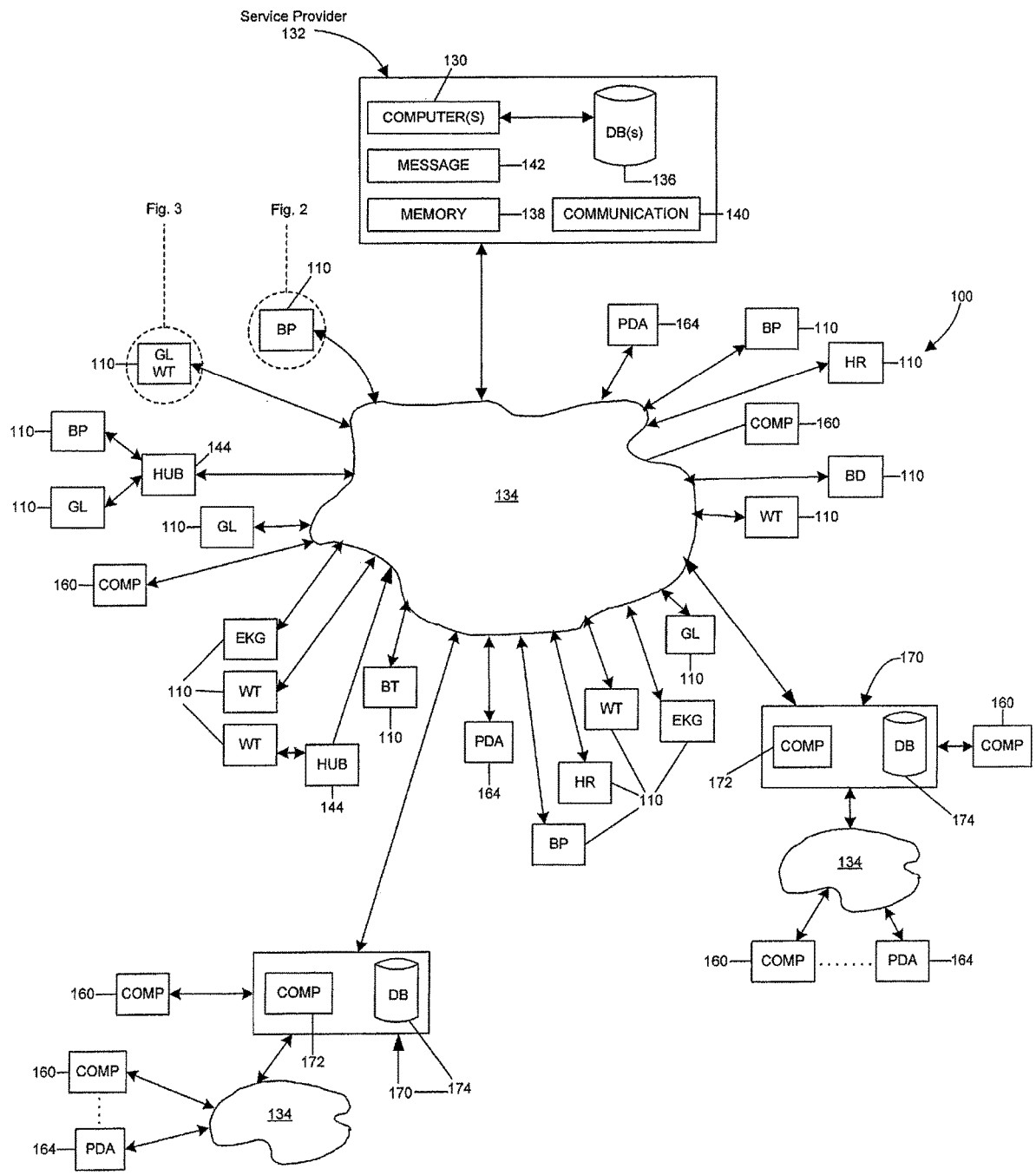
FIG. 1 is a block diagram of a health care management system of a type described in application Ser. No. 11/356, 739.

FIG. 1 depicts an embodiment of a health care management system of a type described in application Ser. No. 11/356,739. The system 100 comprises a plurality of monitoring devices 110 (shown in more detail in FIGS. 2 and 3) that obtain health-related information of subjects (not illustrated) and at least one computer 130 of a service provider referenced generally by 132 which communicate over a network 134. The monitoring devices 110 provide health-related information of subjects and messages to a service provider computer 130, and a service provider computer 130 provides messages and health-related information to the monitoring devices 110. The service provider 132 also includes at least one database 136, memory 138 and a communications unit 140. Health-related and other information is stored in the database(s) 136 and/or memory 138, including information relating to subjects, groups and organizations such as care groups, climatic data, messages, etc. Some of the information stored by service provider 132 may be provided by computers 160, PDAs 164 and computer systems 170 of, e.g., care groups, care provider groups, service providers, payors, etc. The communications unit 140 may comprise any suitable hardware and/or software for managing communications over the network 134 between the service provider 132 and the monitoring devices 110, computers 160, PDAs 164 and computer systems 170. The computers 160, PDAs 164 and computer systems 170 comprise communications units compatible for communicating with the service provider 132.

The at least one computer 130 may communicate subject information or other information to service providers 132, computers 160, PDAs 164 and computer systems 170, and to one or more monitoring devices 110 via network 134. One or more of the recipients may be a care group or care provider group that maintains a database 174. For example, a medical group or physician may maintain a database of patients under their care, and may also have access to the patient information obtained with a monitoring device 110.

Figure 3:
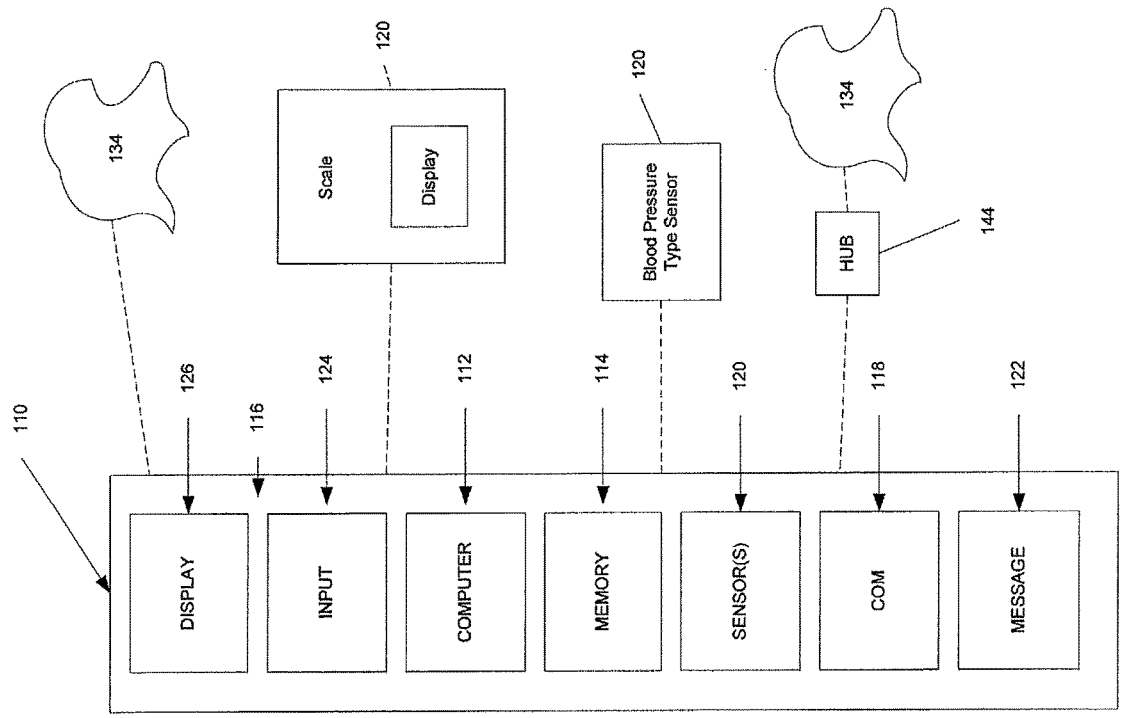
FIGS. 2 and 3 are schematic, block diagrams of embodiments of monitoring devices that may be used in the systems depicted in FIGS. 1 and 4.
Figure 2:
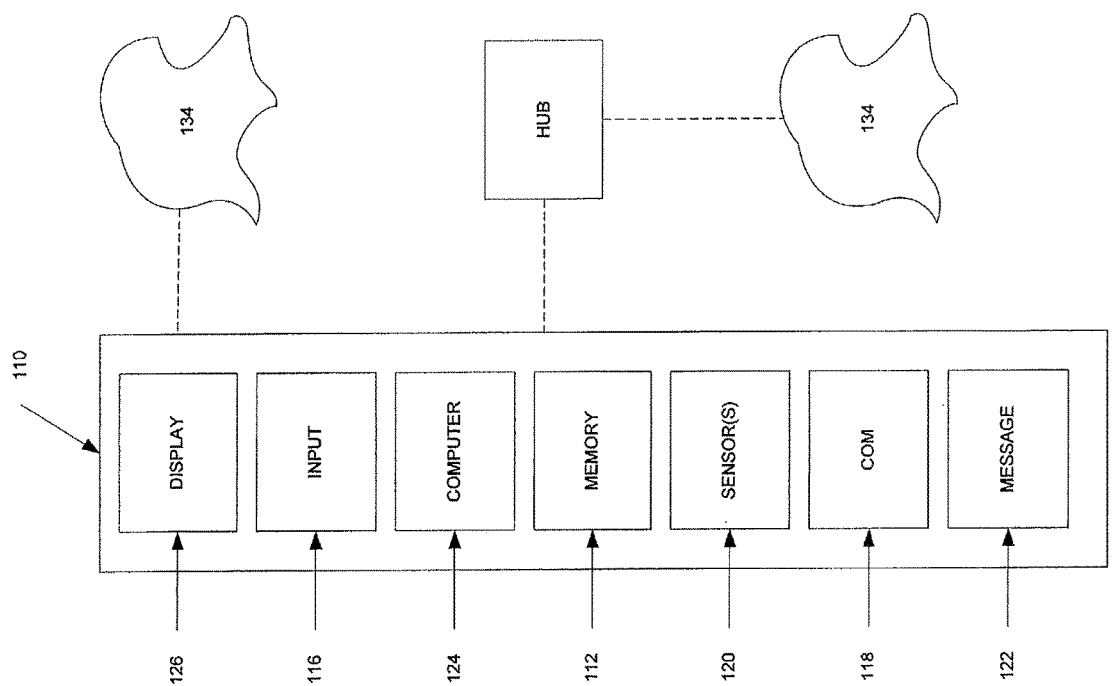

In one embodiment, as depicted schematically in FIGS. 2 and 3, the plurality of monitoring devices 110 each includes or has associated therewith one or more of the following: a computer 112, e.g., an electronic controller; a memory 114; a user interface 116 for a user to input and view information; a communications unit 118; one or more sensors 120 (FIG. 3 shows two sensors); a messaging component 122; a software or hardware implemented clock and/or a calendar (not shown) which associates a time and/or date with health-related information of a patient received by the monitoring device; a power source (not shown), such as batteries and/or an AC plug and/or adaptor and/or battery charger, etc.

The computer 112 may comprise any suitable programmed microprocessor, preferably implemented on an integrated circuit. Memory 114 may comprise any suitable volatile and non-volatile electronic memory. The user interface 116 (FIGS. 2 & 3) includes an input device 124, such as buttons or a keypad or a keyboard and/or a touch device, mouse, etc., and an output device 126, such as a display device, e.g., a liquid crystal device. Messages may be composed on a monitoring device through use of the input device, e.g., by direct inputting of characters, or by selecting characters or graphics or items presented by or stored in the monitoring device, and in other ways. The memory 114 stores health-related information of a subject, information input via the input device 124 and information provided by the remote computer 130, and device and user information, e.g., a user identification ("user ID"), device identification ("device ID"), e.g., a serial number, etc.

The communications unit 118 may comprise any suitable software and hardware for managing communication between a monitoring device 110 and a computer 130, over the network, and with or without an intermediary transmission device such as hub 144 described below. The communications unit 118 may also comprise any suitable hardware and software for managing communication between a monitoring device 110 and a sensor 120. Such software and/or hardware is known in the art or described in the cited patent applications. For example, communications unit 118 may utilize Bluetooth technology to manage communications between the monitoring device and a sensor or sensors, and between the monitoring device and an intermediary transmission device. The communications unit 118 or the intermediary transmission device manages network communication, including network protocols, e.g., TCP/IP. The communications unit 118 may comprise or communicate with devices such as a modem, and/or a communications port such as a USB port, an RS 232 port, a serial or parallel port, through RJ-11 jack/ADSL/cable modem, etc.

The messaging component 122 (FIGS. 2 and 3) of a monitoring device 110 manages messages sent and received by the monitoring device over the network 134, and may comprise any commercially available software and/or hardware. For example, where the monitoring device is a portable computer, or laptop computer, or a desktop computer, the messaging component may be Microsoft Outlook software, or other commercially available software, and where the monitoring device is a portable device, e.g., or a PDA device, the messaging component may be Microsoft Mobile Outlook software or other commercially available software. Messaging software is also described in the cited applications or software described in the cited applications. However, the software and hardware may be any suitable software and hardware. The service provider 132 also includes one or more messaging components 142 that are compatible with the messaging component(s) 122 in the monitoring devices 110. For example, the messaging component 142 may comprise hardware and/or software for supporting messaging between the service provider 132 and the monitoring devices 110, e.g., one or more servers running Microsoft Outlook software or other commercially available software. However, any suitable compatible hardware and/or software may be used to implement the messaging components 122 and 142.

Sensors 120 (FIGS. 2 & 3) that are associated with monitoring devices 110, e.g., incorporated in a monitoring device or wirelessly coupled (e.g., using Bluetooth, radio frequency, infrared, sonic, etc., technology) or coupled by wire to a monitoring device, etc., may be classified by type based on the type of health-related information the sensor provides. Examples of types of health-related information provided by sensors include the information described above. A monitoring device 110 may have one sensor associated therewith or a plurality of sensors, e.g., a blood pressure type sensor and a weight type sensor (FIG. 3), or a blood pressure type sensor and a heart rate type sensor, or a glucose level type sensor and a weight type sensor, etc. Where more than one sensor is associated with a monitoring device, the sensor types may be related, e.g., a subject with diabetes may also be overweight, and in that case, the subject's monitoring device or devices would have associated therewith a glucose level type sensor and a weight type sensor, or a subject with high blood pressure may have a heart condition and an EKG type sensor and/or a heart rate type sensor may also be provided for that subject. In the example represented in FIG. 1, the type of sensor or sensors associated with a monitoring device 110 are designated by: BP for blood pressure; HR for heart rate; BT for body temperature; WT for weight; EKG for electrocardiogram; EEG for electroencephalogram; and GL for glucose level. As mentioned, a monitoring device 110 may be multi-purpose, e.g., associated with a plurality of sensors for measuring different types of physiologic parameters, or different types of devices 110 may be associated with a subject for measuring different types of physiological parameters, such as a weight scale to obtain a user's weight, a blood pressure cuff to obtain a user's blood pressure, a glucose monitor to obtain a user's blood glucose level, etc., or any combinations thereof, such as a combined glucose and blood pressure measurement device 110. Monitoring devices and sensors may be provided for other types of health-related information, and FIG. 1 is exemplary in depicting some of the possible monitoring devices and sensors that may be used in the system.

Figure 4:
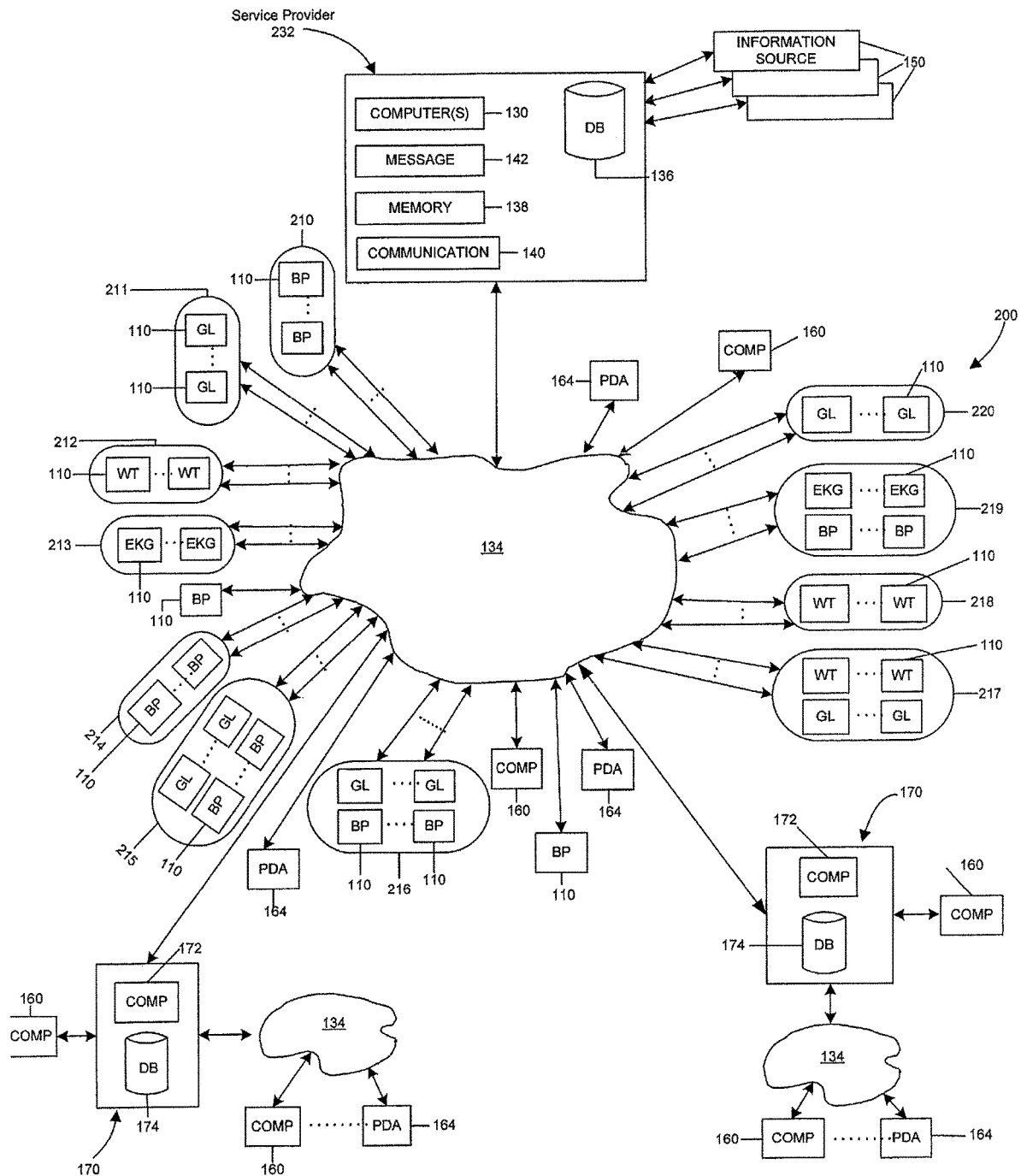
FIG. 4 is a block diagram of a health care management system according to an embodiment of the invention.

FIG. 4 illustrates a system 200 that includes monitoring devices 110, a service provider 232, information sources 150, computers 160 and systems 170. According to one embodiment, communication between monitoring devices 110 and the service provider may proceed as follows: wireless Bluetooth from a monitoring device 110 to a hub 144, and secure HTTPS from the hub to the server 130, which accesses the database 136 via a LAN. In an alternative embodiment, the monitoring devices 110 and the server 130 communicate via HTTPS without the intermediary hub 144. HTTPS is a non-proprietary protocol that is publicly available, and database access may be provided by any suitable database management software. The server 130 may function as a gateway that allows messages to be sent to and from the monitoring device 110.

System 200 depicted in FIG. 4 is similar to system 100 depicted in FIG. 1. One difference is that the service provider 232 in FIG. 4 arranges monitoring devices 110 with the same type of sensor or sensors into groups, e.g., "peer" groups, illustrated by the enclosed areas 210-220. Also, the service provider database 136 in FIG. 4, described below, differs from that in FIG. 1. One reason for arranging monitoring devices in groups is to manage messages originating from within a group destined for one or more other monitoring devices in the same group and/or sub-group. For example, in groups 210 and 214, the monitoring devices 110 in the respective groups each are associated with a blood pressure type sensor, and in group 211, the monitoring devices 110 in the respective groups are associated with glucose type sensors. Some groups include monitoring devices associated with two different types of sensors, e.g., groups 215 and 216 (BP & GW), 217 (WT & GL), 219 (EKG & BP).

The service provider 232 (FIG. 4) may arrange more than one group of monitoring devices with the same type or types of sensors. For example, in groups 210 and 214, each of the monitoring devices 110 is associated with a blood pressure type sensor. In such cases, such groups may be associated with different care groups, or organizations, e.g., HMO #1 and HMO #2, or Insurer #1, Insurer #2, or separate groups may be formed within the same organization based on other criteria.

Subjects may be identified as candidates for a monitoring device as described in cited application Ser. No. 11/356,739 as follows. Subjects are identified who are actually or possibly in need of care, and provided with monitoring devices with the goal of detecting worsening or acute situations and intervening early before more serious and more expensive care is needed. According to the cited application, health care practitioners, e.g., practitioners other than medical doctors such as nurses, medical assistants, paramedics, trained staff, may determine when to intervene and encourage or arrange for health care to be provided to monitored subjects by appropriate health care professionals. According to the cited application, subjects are identified for monitoring based on data such as medical history and/or initial measurements related to one or more health-related issues, e.g., high blood pressure. Health-related information of such subjects, including physiologic information, is provided to a database. The database processes the information and provides data which indicates, or from which can be determined, whether a subject is a candidate for monitoring. As described in the cited application, groups are formed of subjects with the same or similar health-related issues, and the concerned subjects are notified.

Cited application Ser. No. 11/356,739 describes enrollment of subjects, identifying subjects to be monitored, data acquisition from subjects by monitoring devices and/or from measurements made in health care professionals' facilities, processing of data to form groups of members with like medical conditions and/or degrees of seriousness of a medical condition, and/or to identify candidates for intervention, e.g., by means of automatically generated alerts, and/or to notify such members and/or health care professionals attending to such members, etc.

In the systems 100, 200 depicted in FIGS. 1 and 4, a service provider computer 130 also communicates with computers 160 (desktop, portable, laptop, etc.), PDAs 164, computer systems 170 and other devices of parties related to a subject or subjects such as family, care givers (e.g., family members, partners, friends, professional care givers, etc.), various providers including health care professionals and non-professionals (e.g., physicians, physician assistants, nurses, nutritionists, nurse's aids, therapists, exercise coaches etc.), care groups, suppliers of consumables used with the monitoring devices (e.g., glucose monitoring strips, insulin for insulin pumps), insurers and payors, etc. The type of information that may be communicated varies with the relationship between the party and a subject, HIPAA requirements, if any, data access permissions, etc. Generally, computers 160, PDAs 164 and computer systems 170 may be provided with information from service provider 132, 232 via a web server computer 130 over network 134, e.g., the Internet, or alert type information issued by a service provider computer 130 via a messaging system such as conventional email, e.g., over the Internet, or by computer controlled telephony or facsimile, or by an individual at the service provider 132, 232 placing a telephone call or sending a facsimile to a party related to a subject.

In the systems 100, 200 depicted in FIGS. 1 and 4, the service provider computer 130 also communicates with computer systems 170, e.g., of health care providers, care groups, organizations such as insurers, payors, health plans, fitness centers, etc. The computer systems 170 may include one or more computers 172 and databases 174 for storing information relating to subjects, e.g., provided by the service provider 132, 232 based, e.g., on information the service provider collects from monitoring devices 110, computers 160, PDAs 164, sources of information 150, computer systems 170, etc., where such information may include the information described above. The computer systems 170 may provide access to information stored by the computer system to user computers 160 and PDAs 164 over the network 134, or a LAN, etc. The type of information that may be communicated varies with the relationship between the organization and the user, HIPAA requirements, data access permissions, etc.

In some embodiments, in systems 100 and 200, a monitoring device 110 communicates with a service provider computer 132 over the network 134 via an intermediary transmission device or hub 144. In some embodiments, a monitoring device 110 communicates with a computer 130 over the network 134 without an intermediary transmission device 144.

The type of health-related information stored by service provider 132, monitoring devices 110, computers 160, PDAs 164 and computer systems 170 includes contact information of subjects, care givers, care providers, facilities, service providers, emergency contacts, medications, allergies, medical histories, clinical evaluations, family histories, hospitalizations, medical visits, and specific physiologic measurements such as weight, blood pressure, or glucose levels, text or picture messages.

Where an intermediary transmission device 144 is used, the monitoring device(s) and the transmission device communicate with suitable wireless technology, such as an RF carrier, e.g., Bluetooth technology, although other wireless, or wired, communications may be used. The intermediary transmission device 144 generally acts as a hub or base for one or a plurality of monitoring devices 110, e.g., a plurality of monitoring devices with different sensors or of different types, or devices with the same type of sensor or of the same type used by different subjects, e.g., in the same household. For example, the transmission device 144 may include a transmitter and/or a receiver for communicating wirelessly with one or more monitoring devices 110 and a modem and/or a jack, connector, or other port for connecting to the server computer 130 over the network 134, such as a cellular telephone network, the public telephone network, the Internet, or any other network. The configuration and operation of monitoring devices and transmission devices is described in more detail in patent applications referred to above. This embodiment is described in more detail in the cited applications.

Where a monitoring device 110 communicates with a computer 130 without an intermediary transmission device 144, the monitoring device may be configured and operate as a PDA, portable computer, desktop computer, cell phone, etc. to communicate with the service provider computer 130, display information on the display device 126, receive and process information input by the input device 124. Also, a monitoring device 110 may be a PDA, portable computer, PC or cell phone or other device that may or may not include specifically configured hardware but does include at least some software that is specifically configured to perform some of the functionality described herein. Such devices may include at least some hardware and some software that is specifically configured to perform the functions described herein, e.g., obtain health-related information of a subject via one or more sensors 120, and store, process, display, and communicate, etc. such information. FIGS. 1 and 4 are exemplary in depicting some of the possible monitoring devices that may be used.

Information stored by service provider 132 may be provided by computers 160, PDAs 164 and computer systems 170 of, e.g., care groups, care provider groups, service providers, payors, etc., and additionally by information sources 150 (e.g., news organizations, advertising organizations, manufacturers and distributors of products that may be related to health-related issues, organizations maintaining electronic health (medical) records ("EHRs"), organizations providing health-related or other data for EHRs, etc.).

As mentioned, FIG. 4 illustrates a system 200 that includes monitoring devices and a service provider similar to the embodiment depicted in FIG. 1, but in which the service provider 232 arranges monitoring devices 110 with the same type of sensor or sensors into peer groups 210-220, and manages messaging between and among subjects based on memberships in a group or groups. The system 200 provides a peer-to-peer network for monitoring devices 110 in the same group or sub-group.

A number of monitoring devices 110 may be grouped together as described herein, and messaging between and among monitoring devices 110 may be restricted to monitoring devices in the same peer group, or to sub-groups within a larger peer group. According to one embodiment, an alert message, or motivational message can be generated manually or automatically by a monitoring device 110 or a service provider computer 130, and transmitted to a member or members of the same group. As discussed above, this may be done on an interactive or real time basis. For example, messages can be triggered by a specific event, e.g., an emergency message can be transmitted from a monitoring device 110 with a blood pressure type sensor of a cardiac patient to other members of a cardiac peer group if the patient's heart rate or blood pressure readings fall into a certain range, or a motivational message can be transmitted from all members of a weight loss peer group to a specific member if the subject's weight or daily caloric intake fall into a certain range, as measured by the monitoring device 110. In another embodiment, messages can be triggered by consumable tracking parameters, e.g., an emergency message can be transmitted from the monitoring device of a diabetic patient to other members of a diabetes group if the level of insulin remaining in the reservoir of a patient's insulin pump reaches a certain level, or, similarly, an order can be transmitted from the monitoring device 110 to a pharmacy or other supplier (represented, e.g., by computer 160 or computer system 170), to automate the ordering of additional insulin.

As described in cited application Ser. No. 11/356,739, a service provider may facilitate management of various types of health problems, such as high or low blood pressure, glucose levels, weight, etc., and subjects may be grouped based on health related issues. For example, the health of a group of subjects belonging to a care group may be managed. As described in application Ser. No. 11/356,739, subjects are enrolled in a coordinated care group, and certain subjects are identified for monitoring, including forming groups with like medical conditions, health related classifications, degrees of seriousness of a medical condition and/or phase of a particular program.

As described in cited application Ser. No. 11/356,739, initial physiological measurement data related to each of a plurality of people in a group is received. In general, the group of people may be any group of people, such as members of a managed health care organization, members of a fitness organization, members of an institution, subscribers to an internet service provider, all citizens of a state or country, all members of a family, or other group. The physiologic measurement data may be any data indicating a physiologic, health or other condition or state of an individual. Initial measurements may be received to provide a baseline health condition of the person. Additional physiological measurement data related to each person in a sub-group of the group of people may be received. In general, the persons in the sub-group have an initial physiological measurement that satisfies a criterion, such as a first criterion, which may be a value. A computing device may be used to automatically determine that the initial physiologic measurement satisfies the first criterion. For example, a sub-group of a group of persons may be created for individuals having a blood pressure measurement above or below a certain initial criteria. The additional physiological measurement data may be obtained using a portable device, such as a medical monitoring device that is provided to each person in the sub-group. The additional physiological measurement may relate to the sub-group, such as in the example above, additional blood pressure readings, or other physiological measurement. The additional monitoring may be received according to a frequency or period as necessary for the sub-group. Additional monitoring may be based on a treatment regimen that is appropriate for the sub-group.

According to an embodiment of the invention, each person in the sub-group may be contacted when an additional physiological measurement data obtained by a portable device satisfies a second criterion, which may be a value, such as a higher or lower reading than the initial first criterion. A computing device may be used to automatically determine that the initial physiologic measurement satisfies the second criterion. The additional physiological measurements, when compared to a first and second criterion may provide an indication of a change in a person's health, physical or physiological condition. The person, or representative or other contact, may be contacted in connection with the reading. The contacting may be via an electronically delivered message, such as a text message sent to a portable device, email, voicemail or other message, or a telephone call from a health care manager or other individual associated with providing managed health care. Prior to the contact, an individual, such as a health care provider, care coordinator, health care professional, such as a nurse, doctor, physician's assistant, or other interested individual may review the additional physiologic measurement that satisfies the second criterion, or other additional physiologic measurement, e.g., to ensure that intervention is appropriate. In general, the method may be provided by health care practitioners, which may include doctors, but is typically provided by a nurse, physician's assistant or other health care provider or professional.

An embodiment of enrollment of monitoring devices and screening of subjects for enrollment in monitored groups is described further below.

Information related to subjects and other information which can be used to determine eligibility of subjects for enrollment in a monitored group or groups may be stored in a service provider database 136. A monitored group may be constituted by subjects from a single organization such as a care group, or from subjects associated with different organizations or not associated with any organization. In one embodiment, membership in a monitored group is limited to subjects from the same care group. In this embodiment, subjects with the same or related health issues who are monitored using the same type or types of sensors are selected for membership in a monitored group.

FIG. 5 depicts exemplary data structures 300, 302, 304 and 306 maintained in a database 136 of service provider 232 (FIG. 4). The data structures may comprise data records arranged in tables that include all or combinations of the following and other fields: user (subject) ID, device ID or IDs, user name, address, telephone number, sensor type or types, organization ID or IDs, message group or groups, and other information such as subject medical information, sensor data, EHR information, SSN, password, PIN, insurance company, etc. The information may be arranged in a relational database defined by tables, e.g., a subject table 300, a device table 302, care giver table 304, a message group table 306, and other tables.

Additional information related to subjects may be stored in records and/or documents maintained in one or more databases and/or document systems. Such information may include data provided by monitoring devices (e.g., sensor data), patient EHRs, clinical information, climatic information, news, current events, health-related alerts, etc.

In an embodiment, the data structures 300, 302, 304 and 306 may comprise data records arranged in tables where a field or fields comprise database keys. For example, in table 300, field "user ID" may comprise a primary key to uniquely identify records in table 300. As another example, in table 300, field "device ID" may comprise a foreign key to cross-reference data in a relational table, e.g., with a primary key "device ID" in table 302.

Figure 6:
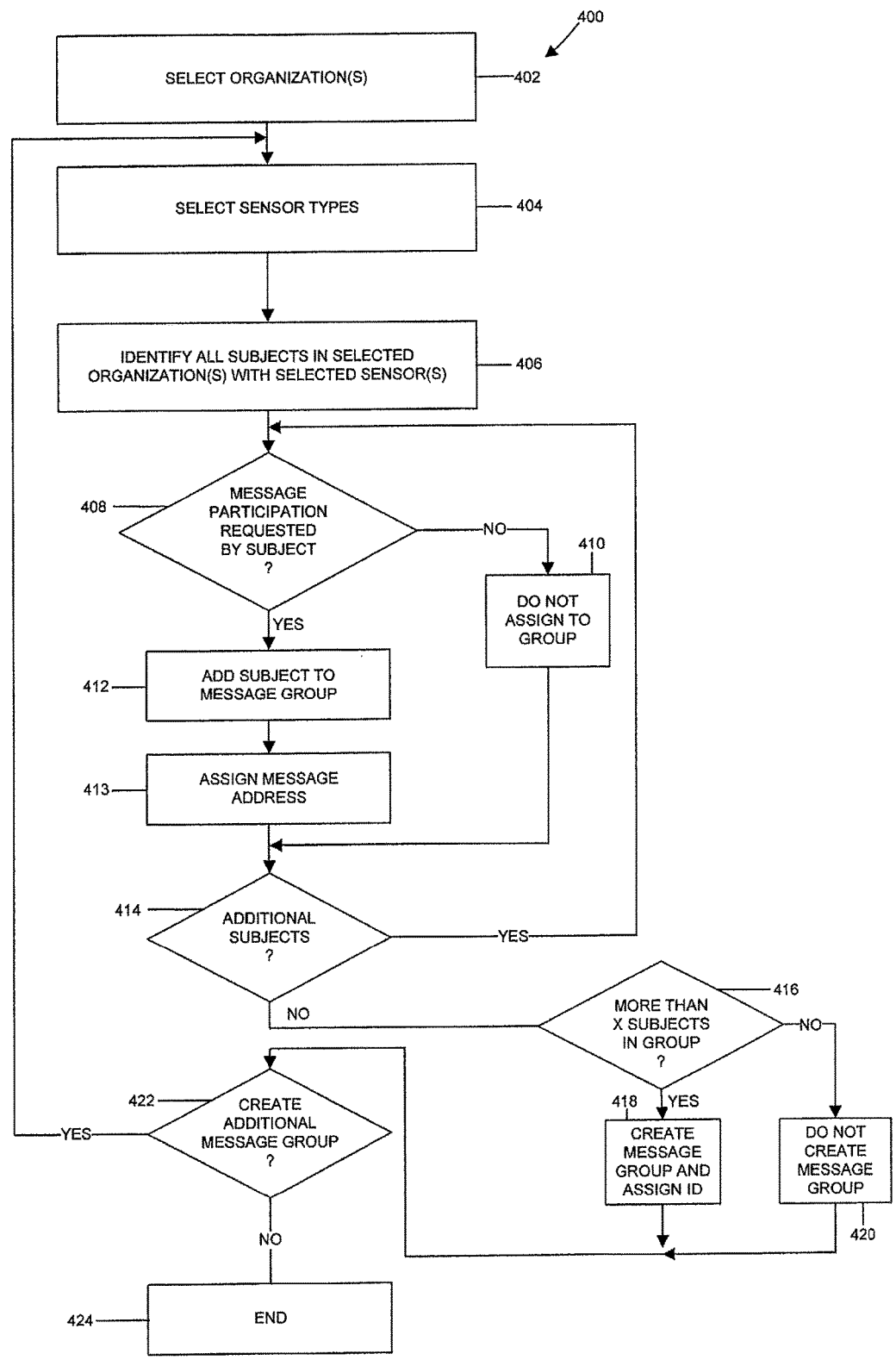
FIG. 6 is a flow chart illustrating a process for creating messaging groups of monitoring devices in the system depicted in FIG. 4 according to an embodiment of the invention.

FIG. 6 provides a high level illustration of a process 400 for enrolling subjects in a messaging group. As discussed above, a messaging group may be formed of members of a single organization or from members of a plurality of organizations, and/or unaffiliated subjects. In block 402, a service provider selects the organization or organizations, e.g., care groups, or unaffiliated subjects expressing an interest in joining, from which members of one or more message groups are to be drawn. In block 404, the service provider selects a sensor type or types for a message group within the selected organization(s). For example, a blood pressure sensor may be selected. In block 406, all subjects within the selected organization(s) having a monitoring device and the selected associated sensor(s) are identified. Block 408 determines whether a subject identified in block 406 has agreed, requested or otherwise consented to be in a message group, either at all or by sensor type. If in block 408 determines that a subject has not opted to be in a message group at least for the selected sensor, then the subject is not identified as a member of the message group (block 410), and if the subject has opted into a message group for at least the selected sensor, the subject is identified for inclusion in the message group for at least the selected sensor in block 412.

In block 413, a message address is assigned to or selected by a subject. As mentioned, the address may be anonymous so as not to reveal the identity of the subject. For example, the Internet email address format may be used, which includes a user name (can be anonymous) followed by @ and a domain name. However, any suitable address convention or format may be used.

Block 414 of the flow depicted in FIG. 6 determines if there are additional subjects in the selected organization that have not yet been tested for a determination of whether they have opted to participate in the or a message group. If so, the flow loops back to block 408, and if not, the flow proceeds to determine in block 416 if there are sufficient subjects to form a message group. For example, an organization may determine that it will form a message group only if there are more than X participants. A message group is created in block 418 and a message group ID is assigned if there are more than X subjects, otherwise not (block 420). In either case, the flow determines in block 422 if the selected organization has selected an additional message group for possible formation, and if so, the flow loops to block 404, and if not, ends (block 424).

A message group may be formed by creating records or tables in a database such as those illustrated in FIG. 5, which associate a monitoring device or devices of a subject with a message group. An example of such a record or table 306 is depicted in FIG. 5. Table 306 includes a field 310 for the messenger group, a field 312 for a device ID, a field 314 for a sensor type, a field 316 for a user name, a field 318 for organization ID, etc. As mentioned, records 300, 302, 304, 306 may constitute tables in a relational database. Tables 300, 302, 304, 306 may be populated with data in any suitable way. For example, data may be provided by a subject via a questionnaire, paper or on-line, via telephone, automated IVR or to a customer service representative, by an organization which has previously compiled relevant data and a process such as flow 400, etc.

In one embodiment, relevant data may also be arranged in a data structure 330 (FIG. 7) as a matrix for each subject on a service provider wide or organization wide basis. For example, matrix 330 depicted in FIG. 7 includes a row 332 for each monitoring device 110 and columns identifying organization(s), sensor types, message groups, etc. A one bit flag indicates whether a monitoring device (device ID) in the row is associated with a particular care group, sensor, etc.

Matrix 330 may be populated from the flow 400 depicted in FIG. 6. Selecting the organization(s) in block 402 creates a matrix in which all of the IDs of all of the monitoring devices 110 in all of the selected organization(s) are loaded into column 333 of the matrix, and the IDs of the selected organization(s) are loaded into respective column 334, 336 of the matrix. The message group IDs assigned in block 418 are associated with column 338 and the sensor types are associated with column 340, 342, etc.

The matrix is populated for each device ID by one bit flags to indicate which organization(s) monitoring device (device ID) in the row it is associated with, and which sensor types are associated with the monitoring device in the row. A device is associated with a message group based on the flags in the organization(s), sensor type and the opt flags in column(s). The Tables 300, 302, 304, 306 and/or matrix 330 may be used in routing messages from monitoring devices 110 only to other monitoring device associated with at least one sensor type in common.

Figure 8:
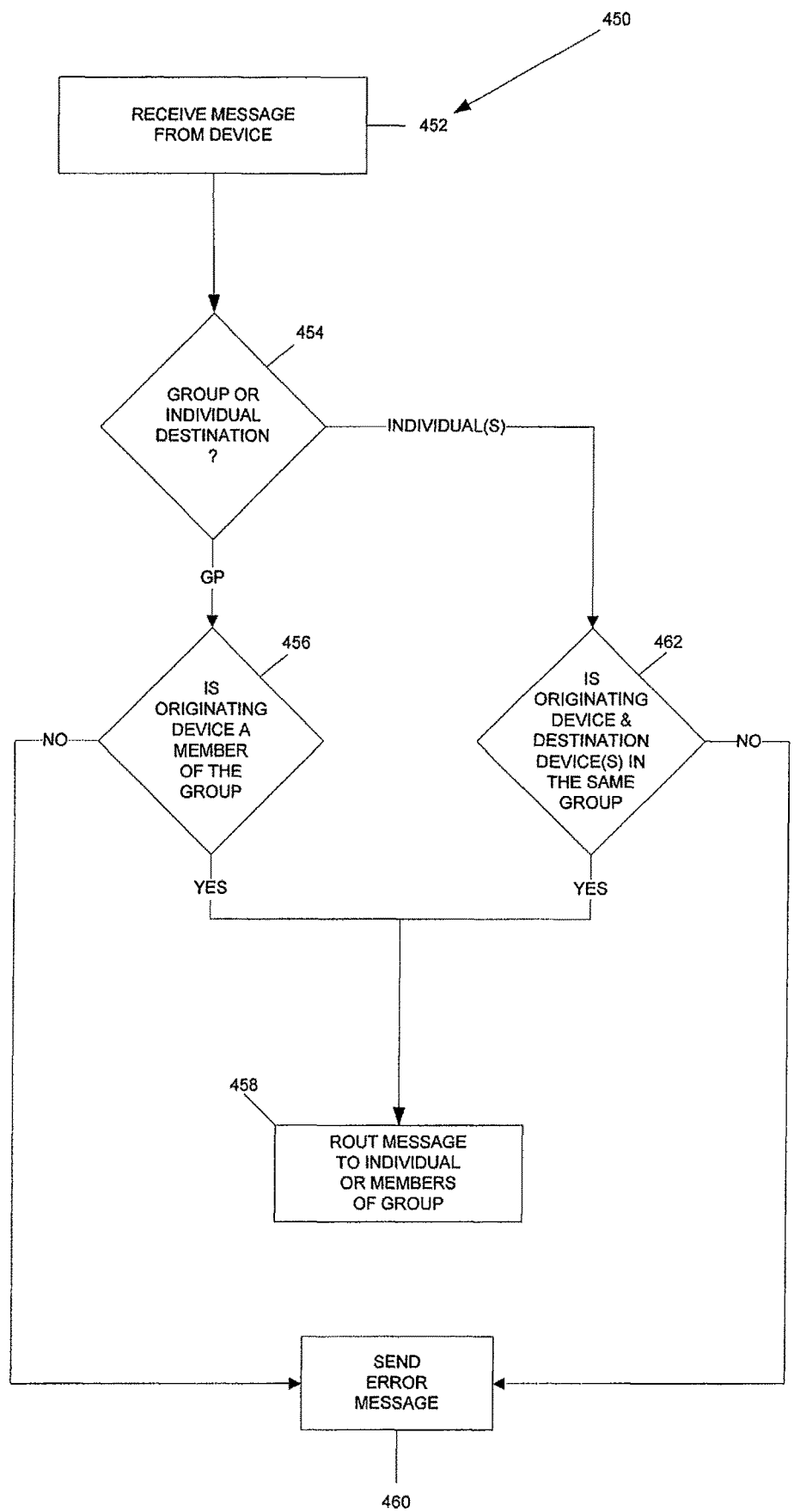
FIG. 8 is a flow chart illustrating routing of messages from monitoring devices in the system depicted in FIG. 4 according to an embodiment of the invention.

Routing of messages originating from monitoring devices 110 may be restricted based on a matrix or database records or tables. An exemplary flow 450 is depicted in FIG. 8. A message is received from a monitoring device in block 452. The message includes information identifying individual destination monitoring devices, groups of monitoring devices or all monitoring devices in a group. Block 454 determines whether the destination is to an individual monitoring device or a group of monitoring devices. If to a group, block 456 determines whether the originating monitoring device is enabled to transmit a message to the group, and if so, the message is routed to all members of the group in block 458. If the originating monitoring device is not enabled to transmit messages to the identified group, an error message is returned to the originating monitoring device in block 460. If block 454 determines that the message destination is for one or more specific monitoring devices, block 462 determines if the origination and destination devices are in the same message group. An error message is returned to the originating monitoring device in block 460 for each destination monitoring device not in the message group, and the message is routed to each identified destination in the message group in block 458.

An "envelope" icon or other message indicator may appear on the display 126 of the monitoring device 110, or an audible message indicator alert may sound when such information is received. Upon selection of a messages menu item, an appropriate messaging screen is displayed. The messaging screen may provide a list of opened and unopened messages, which may be selected by the subject for viewing. Upon selection, the contents of the selected messages are displayed. As noted above, messaging may vary. The messaging may be a prompt for information, such as a compliance query, which shows a message from, e.g., computer 130, a service provider 232, or a recipient, inquiring whether the user has taken medication. Similarly, the messages may inquire regarding use of the device, which may serve as a gentle reminder for the user to use the device 110 more often. Other free text messages relating to received data may also be sent to the device 110.

Health-related information may be provided by monitoring devices as described in a cited application. For example, a monitoring schedule may be defined by a subject or health care provider for initiating operation of a monitoring device to obtain sensor data and communicate the sensor data to the service provider 232. In one embodiment, sensor data is automatically obtained based on time, e.g., hourly or daily, which may be adjusted dynamically based on the previous reading, i.e. a blood pressure reading taken daily may be changed to an hourly reading if a previous reading is above a certain value. In another embodiment, sensor data is taken manually at the direction of the patient.

A monitoring device 110 retrieves sensor data from the associated sensor. The sensor data may be stored in memory 114 (FIGS. 2 and 3) on the monitoring device 110 and then transmitted over the network 134 based on pre-defined automated or manual transmit instructions. Stored messages may be transmitted at the same time, or messages may be composed and transmitted similar to current email, or composed, stored and transmitted with other information such as sensor data. The health-related information and messages are routed to the service provider 232 over the network 134, and the service provider 232, re-routes messages to authorized subjects, stores health-related information, etc.

For example, in a case where health-related information of subjects may be distributed by service provider 232 in accordance with HIPAA requirements and subject authorizations.

In one embodiment, alert ranges may be defined by a patient or health care provider to determine when health-related information such as weight, blood pressure, or glucose levels, are transmitted. For example, a subject may choose to have a monitoring device 110 transmit a glucose reading only if it falls below a certain value, or a health care provider may choose to have a monitoring device 110 transmit a blood pressure only if it rises above a certain value.

Measurement data, tracking data, and messages transmitted by monitoring devices 110, can be selectively transmitted with different urgency levels, e.g., a motivational message would be marked as low priority, while a high blood pressure reading would be marked as urgent.

Communication of health-related information is preferably secure and/or encrypted over the network 134. For example, the end to end communication is encrypted throughout, and each session is authenticated and validated prior to sending any information. Any suitable protocol may be used for communication between monitoring devices 110 and a service provider computer 130.

Computer 130 may communicate subject information or other information to various recipients as depicted in FIGS. 1 and 4 via network 134. One or more of the recipients may be a health care provider (represented, e.g., by 170) that maintains the database 174. For example, a physician may maintain a database of patients under his or her care, and may also have access to the information obtained with a monitoring device 110. A recipient may also be a family member, interested individual, or any other person who may wish to receive the monitored subject's information, as represented, e.g., by computers 160 and PDAs 164.

A recipient may also communicate with a monitoring device 110 via the network 134 and computer 130 for example to supply information or questions in response to received subject information. Such communication is controlled by the service provider 232 and limited to recipients and subjects who are related. For example, the service provider provides information from a recipient physician to a subject who is a patient, or from a recipient family member of a subject, etc.

A subject may register a monitoring device 110 as described in cited application Ser. No. 11/108,355. Cited application Ser. No. 11/108,355 also describes a protocol for taking a physiologic measurement with a monitoring device 110.

The subject's information may be communicated from the monitoring device 110 to the computer 130 via network 134 at about the time the measurement is taken. The monitoring device display 126 can include indications that the subject's information is being transmitted, such as a transmission or connection icon. When the computer 130 has been reached, confirmation that the information has been received by the computer 130 may also be indicated on the display 126 of the monitoring device 110. If computer 130 cannot be reached, an indication of the failed communication will be indicated on the monitoring device display.

The memory 114 of the monitoring device can be, for example a 24C256 256 Kbit Serial Electrically Erasable PROM (EEPROM). The memory is accessed via an I Square C (I2C) serial bus. The bus signals required may be a clock input (SCK) plus separate data lines (SDA). Data stored in the Memory can include, for example: system database, multiple measurements, chart data, messages from system, user identification, serial number, time data for the measurements, etc. The monitoring device 110 may include a built-in A/D converter that is used, e.g., to measure the battery voltage.

The intermediary transmission device 144 may be a real time system that is designed as a combination of an interrupt communication system and a polled event handler. The communications sub-system handles RS232 communications (modem) as well as radio frequency communications, Bluetooth or other communication means, with the blood pressure meter or any other device. The transmission device 144 carries out commands to connect via a network, such as the Internet, cellular telephone, public telephone, to computer 130, and acts as a conduit for communications between the computer 130 and the monitoring device 110.

In one embodiment, the transmission device 144 generally has a modem, such as IP568 integrated modem chip. The IP568 is a multi-standard modem for use in telephone based information and telemetry systems. Control of the transmission device 15 is via standard AT commands. The IP568 is V.90 N.92 modem chip with a speed up to 56K baud. The on-chip μController interprets these AT commands and controls an internal DSP, which provides the modem and ancillary functions such as Ring Detection, Call Progress Detection, Hook Switch control and DTMF auto-dialing. In addition to the Modem, device 144 also has a high speed Internet interface (RJ45) which enables device 144 connects directly to the Internet. Device 144 also has an USB interface which can be used for the configurations of the device or other features.

The transmission device 144 can also have a cellular telephone interface, such as a RS232 serial interface. Hardware flow control using RTS/CTS is implemented. The signal lines available are: Transmit, Receive, RTS (Request to Send), CTS (Clear to Send), and Ground. In another embodiment, Bluetooth can be the interface between the sensor device and the cellular telephone where software resident on the Bluetooth enabled cellular telephone will allow for transmission of the sensor data.

Monitoring device 110, e.g., communications unit 118, performs communications functions when an intermediary transmission device 144 is not used.

The monitoring device 110 and the transmission device 144 (collectively a "client device") may communicate with the server computer 130 in a variety of ways. In one embodiment, the client device communicates with the computer using the protocol outlined below. The data may be communicated between the devices in a variety of different ways. In one embodiment, the information is communicated to the server 130 in a datagram or packet that includes at least one actual measurement taken with the monitoring device 110, such as a blood pressure, weight, glucose measurement and the date and time the measurement was taken. Additional information for associating the measurements with a particular user may also be communicated to the server 130, whether in the same datagram or otherwise, such as a unique user identification number, etc., as well as information for identifying the particular type of device being used, such as the device identification number, responses to messages, etc. Various types of information may also be sent to the monitoring device 110 from the computer 130, such as chart data, e.g., coordinates as well as other information for plotting a graphical representation of the measure data, messages (long and short form), etc.

As discussed above, computer 130 may access one or more databases which store information of the type described herein, e.g., subject data, health and medical condition data of individual patients, health and medical condition data in general, and/or drug tests, clinical evaluations, data, etc. Computer 130 and/or other computers may access, analyze and process such data in connection with a specific health issue or condition, etc. Information from such a database and other databases may be provided, e.g., for research, analysis or other purposes stripped of user information that may be used to identify particular users, such as the subject's name, address, identification number, etc. Subjects may enter into monitoring devices 110 demographic information and other information that may be included, e.g., with other patient information for, e.g., analysis and research purposes. Subject information may also be used in connection with the provision by a remote computer and appropriate databases of targeted messages, e.g., health related news, alerts, advertising, etc. For example, where a monitoring device supplies blood pressure information, the data may be used to identify the patient associated with the monitoring device as a candidate for a hypertension drug, etc. Such a patient may be supplied with an alert of extreme high or low temperatures, or ozone content, e.g. based on a geographic position. A monitoring device that supplies respiratory information may be identified, for example, as a candidate for an alert of high ozone content, or high air pollution levels, etc. The above or another database may be provided for compliance information.

In this respect, the service provider 232 may provide a website or any graphical interface for accessing information, which will generally be referred to herein as a website, for access to such information and/or for messaging particular monitored users. The particular user's information is preferably made available based on specific user entitlement. For instance, a monitored user may be entitled only to information regarding the user's own monitoring, such as the user's own physiologic measurements, charts, messages, etc. Similarly, a physician, caregiver, family member, or other interested party will have access only to information particularly entitled to, such as the interested party's own patient(s), family member, etc. In this respect, the monitored user may be provided with an interface or some other means for providing access to his or her information for interested parties. Website users may also be provided with information regarding monitored users without authorization provided the information does not contain any personalized information. For instance, the website users may be provided with statistical data regarding other monitored users, such as average readings for other users with similar conditions, compliance, outcomes, etc. In these respects, website users may first be provided with a logon interface screen prompting the user for a user name and a password.

A variety of interested parties may be provided access to information based on specific entitlement. For instance, a health care provider may be provided access to information for the provider's own patients. The term healthcare provider generally includes any individual or entity that is interested in the patient's physiologic measurements, such as a physician, nurse, aid, personal trainer, etc. In this respect, after logging on, the healthcare provider will be provided with a list of menu items, e.g., collectively under a "My Ideal Life" heading, that provide authorized access to specific types of information, such as personal information regarding all of the provider's patients or subgroups thereof, information regarding the provider's patient's readings or subgroups thereof, e.g., reports, messages or action items (interactions) for the particular provider, an online calendar, etc., as shown in FIGS. 2-12 of cited application Ser. No. 11/108,355.

The service provider 232 may provide the interface to a health care provider for the health care provider to manage the health of a group of individuals. Various types of health problems may be managed in accordance with the present invention, such as high or low blood pressure, glucose levels, weight, etc. The individuals may be grouped based on a variety of criteria, such as health related issues, common physicians, common insurance, etc., or a combination thereof. For example, physiological measurement data of a group of individuals may be received and compared to an initial criterion established for a sub-group. The members or persons in the sub-group may be associated with a particular treatment regimen appropriate for their health condition and be provided a monitoring device. Several levels of physiological measurement criteria may be established which correspond to an appropriate intervention for the criteria. For example, in a diabetes sub-group having members that have a particular glucose level that satisfies an initial criteria, one or more criteria may be established for different glucose levels which may have an appropriate intervention.

The system 100, 200 may be used to manage the health of a group of subjects belonging to a coordinated care group. In this embodiment, the service provider 132, 232 is preferably a separate and distinct entity from the care group, insofar as the service provider provides the backend functionality of the service provider system, collectively the computer 130, database 136, message module 142 and the software associated therewith. A group administrator may provide the monitoring devices to its members and monitor the member's health with the interface provided by the service provider. A secondary observer, e.g., other than an actual physician, such as a nurse practitioner, may monitor the members' health to help doctors control the members' health more efficiently. In one embodiment, the interface provides information and alerts as well as other functions for the nurse practitioner to act as a care-coordinator that facilitates coordination between the physician and the patient.

The service provider 132, 232 may maintain the group members' information in a database 136 associated with a computer 130. At least some of the subjects' information, such as the subjects' names, addresses, demographic information, physiologic measurements, etc., may at least initially be shared with the database 136. This may be accomplished to define the coordinated care group. Once the group has been defined, the group administer may provide the monitoring devices to the members of the group, which may then activate the monitoring devices 110 by registering the devices 110 with the service provider 132, 232.

Individual members of a group may be monitored in accordance with a patient monitoring program or treatment regimen. The patient monitoring program generally includes a protocol that serves as a schedule for individual users to take additional physiologic measurements. The protocol may be fixed for the duration of the monitoring period or may vary. In one embodiment, at least one individual is monitored in accordance with a multi phase monitoring program, which may include a first phase for screening individuals for coordinated care regarding a health related issue indicative of a physiologic parameter being monitored, e.g., using an initial criterion as a comparison against physiological measurements to determine whether an individual is appropriate for a coordinated care sub-group (Phase I), a second phase to achieve control of the health related issue (Phase II), a third phase for screening individuals to determine if the health related issue is being controlled (Phase III), and a fourth phase for determining whether the health related issue is being controlled over an extended period of time (Phase IV).

The various phases may be timed accordingly. For instance, the first phase may entail measurements for a period of 8 days or any other time necessary to determine if the individual is a candidate for coordinated care with regard to a health related issue, such as high blood pressure level or other initial criteria for a group in coordinated care. Qualification for coordinated care may be based on a variety of criteria, which includes at least one physiologic measurement exceeding an acceptable threshold. If the individual is a candidate for coordinated care, the individual may be monitored for a longer period of time, fixed or otherwise, or until control of the individual's health related issue is achieved. Control may generally be achieved with coordinated care based on the physiologic measurements taken with the monitoring device 10. That is, the care-coordinator may review the physiologic measurements and/or any alerts derived therefrom and act accordingly in a proactive manner to control the health issue. It is understood that control may be achieved in a variety of ways, such as by prescribing medications or changing dosage, scheduling follow-up visits with a physician, attending to non-compliance issues, etc. Once the time period for control has lapsed, e.g., 6 months, the third phase may be applied to determine if the health related issue is indeed under control and, if so, the fourth phase may be applied to ensure that the health related issue remains under control. The various phases may generally be repeated as necessary until the desired control is achieved. In one embodiment, coordinated care with regard to high blood pressure may be achieved with the program outlined below.

Group membership may be dynamic and based on a member's current health status. For example, if a member's physiologic measurements falls below or is considered better than an acceptable criteria or threshold, the member may be removed from the group. In another example, if more than one physiologic measurement is obtained from the member, one measurement may indicate a relative improvement of a condition which no longer exceeds an intervention or treatment criteria, but second measurement may worsen and exceed another criteria for membership in a coordinated care group or sub-group. In such case, the member may be moved from a first group to a second group. Furthermore, individuals within respective groups can communicate with each other to further assist in education and motivation to achieve desired goals and results.

The service provider 132, 232 may provide a website that includes one or more graphic user interfaces for monitoring physiologic measurements for the members of the coordinated care group. The at least one computer may also provide an interface for use in providing coordinated care for one or more or a group of individuals being monitored with the monitoring device. The interface preferably provides information to a care-coordinator in a manner for the coordinator to act appropriately in a proactive manner. This may be accomplished, for example, by generating alerts for the coordinator based on physiologic measurements and/or action items for the coordinator based on the alerts.

As mentioned any suitable communications protocol and system may be used. A non-limiting example, meant for purposes of illustration, follows.

Communications between a monitoring device and transmitting device (hub) (collectively "client device") and the computer.

Client Device Internet Connection
I. Client devices may communicate with remote computers using an Internet connection using a PPP (Point-to-Point Protocol) connection to the selected ISP (Internet Service Provider).
II. The ISP will provide a national/international, e.g., toll-free, number for initial data access, and may also provide an extensive network of nationwide/international dial-up POPs (points of presence). Initial contact may be with a Contact Center (which may use computers and communication devices different from computers and communication devices that receive, transmit, process, etc. health-related information).
III. The initial, e.g., toll-free number, as well as other information, such as a username, and password, may be loaded into all client devices for registration.
IV. During registration, a local POP access number (or one that is as close as possible to the user's home address), username, and password may be sent to the client device, for further dial-up communications, unless it is remotely or locally reset.

Communication Protocol
I. Communications sessions with the computer may be initiated by the client device requesting either registration or logon to the computer
II. The client device may first resolve the name of the computer using a DNS (Domain Name System) protocol, and use the IP address of the computer for all further communications for the particular session
III. The client device and computer may communicate using TCP/IP, or any suitable protocol, e.g., the UDP (User Datagram Protocol) protocol.
IV. At a high level the sequence for datagram communications in a session is as follows:
  1. Administration;
  2. Readings (sensor reading data);
  3. Measuring (messages, questions and responses); and
  4. Graphing (graphs and charts).

Date and Time Synchronization
I. The client device clock will be set by the computer at the start of every session, i.e., registration or logon
II. The computer may synchronize with a time server on the internet to ensure accuracy
III. The computer may record, e.g., in the database, the home time zone for each client device when it is registered with the Contact Center, or more generally the service provider, based upon the user's home address IV. The computer may convert and transmit all date and time information to the client device from "universal time", e.g., Greenwich Mean Time, to the user's home local time V. The computer may convert and store all date and time information received from the client device from the user's home local time to "universal time"

Language Preference

I. The client device and the computer may store the user's language preference

II. The default language may be US English

III. When the client device is first used or after a reset, the user may be asked to enter/confirm their language selection IV. If the user specifies another language, the computer may store the language preference and download the language preference to the client device during registration Registration I. Preferably, the client device may only be used once it has been successfully registered. On power-up, registration status is checked. If the device is unregistered, the user must go through the registration processes.

II. By making a voice call to a Contact Center the user will receive instructions for use of the system and initially register with the service. The Contact Center may link the user to the serial number of the device in the database.

III. The information collected by the Contact Center may include the full home address of the individual device user, including the postal code, so that a user's local time zone can be determined and stored on the computer. The language preference for the user's client device should also be collected and stored by the Contact Center.

IV. To register the device, the customer may
  a) Make a voice call to the Contact Center or provide the information via the Contact Center web-site and obtain necessary information
  b) Connect the device to computer, e.g., with the toll-free ISP access number
  c) The device will logon and initiate communications to the computer
  d) Information received by the device may include: local access number, username, password, language, date and local time, web address, ports and cellular phone configuration information from the computer.

Logon and Logoff

I. After successful communication, the client device is ready for all communications sessions with the user's unique communications instructions II. To logon, the client device may:
a) Connect to sever, e.g., using a local ISP access number;
b) Initiate communications to the computer;
c) Receive updated information with the local time, etc.; and
d) Send updated device information to the computer.

III. The client device may initiate a normal logoff once all data to be sent from the device has been sent and acknowledged, and no data has been received and validated from the computer for, e.g., 15 seconds. To logoff, the client device
  e) Sends a Logoff Request record to the computer
  f) Receives a Logoff Acknowledgement record from the computer Uploading Blood Pressure Monitoring (BPM) Readings I. Once logged on the client device may start sending any readings that have not yet been successfully uploaded to the computer II. One BPM Reading record may be sent in a single datagram from the client device for each reading taken III. Each valid BPM Reading record sent to the computer may be acknowledged by the computer with a BPM Reading Acknowledged record.

IV. If the BPM Reading record is already in the computer database, no duplicate record will be recorded in the database, but the computer may send a BPM Reading Acknowledgement record to the client device.

Downloading Charts

I. The client device may send a chart request datagram to start the chart downloading process. This may be done anytime after a successful logon and readings transmission. The computer acknowledges with a chart datagram, which includes the number of charts to be downloaded. The device then accepts one chart page datagram for each chart and acknowledges each one with a chart acknowledged datagram. The process ends when the number of charts expected is received and acknowledged II. By default the computer may download all available (up to 10) chart types unless the user has specified otherwise, e.g., on the Contact Center's web site III. The computer may generate a unique Chart ID for each chart that may be stored on the client device as well for unique identification IV. The chart types may include
  a) Systolic
  b) Diastolic
  c) Systolic & Diastolic
  d) Heart Rate V. The chart frequencies may be
  e) Latest
  f) Daily
  g) Weekly
  h) Monthly VI. To provide a graphical representation, e.g., bars, on the client device, the computer may supply a top left and bottom right absolute screen coordinates for each bar. The areas defined by the two extreme coordinates for a bar may be filled in black on the display.

VII. The computer may also transmit the values of the chart labels, such as values for Vertical Label 1 for the top label and Vertical Label 5 for the bottom Label. Similarly, Horizontal Label 1 may be transmitted for the left label and Horizontal Label 2 for the right label.

VIII. The computer may also transmit the exact number of characters to fill each cell, including blanks for positioning properly within the cells.

Client Device Messages

I. Subjects, Professionals, Care Givers, and others may use a form on the service provider web-site to enter and send messages to the client devices II. Two types of messages may be available for these users, a short format and a long format. The short format may have fields for From, Subject, 5 lines of text and two button labels for user response, which will generally be displayed on a single screen of the client device. The long format message will have fields for From, Subject, and 5 lines of text for the first screen on the device, and the second screen will show the Subject and, e.g., six, multiple choice answers. For the long format message the button labels may be standardized on the device to permit moving to the next screen and selecting an answer.

III. Once the user starts to review messages, all messages may be required to be reviewed/answered in order.

IV. Messages may be flagged as Alerts, and these may cause the device to beep when displayed to the device user until they are answered.

Subjects may be screened for enrollment to obtain monitoring devices as follows.

Screening Phases:—patients screened for one week
a. Patients monitor themselves 2 times per day, for 8 days (once in the morning between 6-10 AM and once in the evening between 6-10 PM)
b. Calculation may be based on minimum of 10 readings, and days 2-8 (day 1 should not be included in the calculation of overall MEAN home BP)
   i. If a measurement is missed, or if a day is missed, it will not affect the calculation, all numbers should be included regardless of time
   ii. If there is a need to go back later to verify times, some readings can be looked at twice for inclusion as all are time and date stamped.

After Screening:
a. Patients under drug therapy with office blood pressure ("BP") readings equal to or greater than 140/90 mmHg
   i. If the MEAN home BP is under 135/85 mmHg (<130/80 mmHg for diabetics and kidney disease), patients monitor themselves once every 2 months for 8 days (similar to first week screening method) until the end of the program, and followed up by the nurse once a month. In patients with the low normal range blood pressure (SYS BP less than 120 mmHg), treatment may be reduced or discontinued if there is concern about adverse affects related to hypotension (dizzy or light headed; ex. Pre-syncope). If drug therapy is reduced, patients may be enrolled in the full monitoring program.
   ii. If the MEAN home BP is equal to or greater than 135/85 mmHg 130/80 mmHg for diabetics and kidney disease): Hypertension is confirmed and the patient is enrolled into the full monitoring program.
b. Newly Diagnosed Patients with office BP readings equal to or greater than 140/90 mmHg
   i. If the MEAN home BP is under 135/85 mmHg (<130/80 mmHg for diabetics and kidney disease): The patient is considered to have a normal BP and may be monitored for 8 days (similar to first week screening method) once every 2 months until end of the program, and followed up with by the Nurse practitioner once a month
   ii. If the MEAN home BP is equal to or greater than 135/85 mmHg: Hypertension is confirmed and the patient is enrolled into the full monitoring program Full Monitoring Program:
Patients confirmed with Hypertension may require an appointment with their Primary Care Physician for treatment
a. Patients do not need to have their home BP monitored until after they are seen by their physician
b. After the appointment, the Nurse practitioner should ensure that the details of the Primary Care Physician's treatment plan are entered into the service provider website and that the patient begins to monitor themselves MON WED FRI once between 6-10 AM and once between 6-10 PM each day (it does not matter if a day is missed, or the wrong day is measured for the purposes of the calculation of MEAN home BP)

c. Fixed Follow-up Plan
   i. First 4 weeks of program, Nurse should contact patient once a week for "check-in" (takes 2-4 weeks for drug to take effect)
   ii. Following the first 4 weeks of the program, Nurse should contact the patient once every 2 weeks
   iii. At the midway point of the program; a reevaluation of the follow-up plan should take place to see if 2 weeks or 1 month will suffice for follow-up calls
   iv. If one week's worth of readings is not taken, the Nurse practitioner should call the patient
   v. Depending on compelling indications, the nurse can follow up with the patient more frequently if necessary
d. Every interaction by nurse practitioner with a patient or Primary Care Physician should require data entry into the website. The Nurse practitioner will have forms where she can enter all information gathered directly into the system. This information should include:
   1. Latest office BP reading taken (if any)
   2. Medication changes (type, dosage, frequency)
   3. Clinically significant symptoms/side effects that may affect management/treatment (this should be a free text window)
   4. Hospital visits
   5. Hospital admissions
   6. Emergency room visits
   a. Other notes regarding program from patient perspective
e. The Nurse practitioner may monitor her schedule and readings through a website
f. Monthly reports may be faxed to respective Primary Care Physicians (if able to, including medication changes)
g. Nurse practitioner should ensure that patients do not become alarmed about infrequent "out of range" measurements and should ensure that patient "issues" are addressed appropriately If there are any "Out of Range" measurements, the nurse practitioner should call or otherwise contact the patient and make sure an appointment is made with their Primary Care Physician immediately (if the Primary Care Physician is unavailable, the patient should be seen by a specialist in the CCC or in the emergency room). Such "Out of Range" measurements may include:
a. Reading over 180/110 mmHg
b. Reading under 100/60 mmHg
c. Increase or decrease of more than 40/20 mmHg While the invention has been described and illustrated in connection with preferred embodiments, many variations and modifications as will be evident to those skilled in the art may be made without departing from the spirit and scope of the invention, and the invention is thus not limited to the precise details of methodology or construction set forth above as such variations and modifications are intended to be included within the scope of the invention.

What is claimed is:

1. A heath care management system comprising:
a computer system including at least one database that stores health-related information of a plurality of persons having a plurality of health-related issues, including health-related information of a plurality of persons arranged in at least one group in which each person in a respective group has a health-related issue in common; and
associated with each of the plurality of persons, a device which obtains health-related information from the respective persons, wherein a device of a particular type associated with a particular person relates to the health-related issue of that particular person, and wherein persons within the same group are associated with the same type of device;

each device obtaining health-related information from each of the respective persons for transmission over a network to the computer system, and the computer system generating health-related information for transmission over the network to each device;

each device including a messaging component for sending and receiving over a network or the network at least text messages originated by another device of a person or originated by the computer system, wherein at least text messages among devices are only permitted between devices of the same type.

* * * * *